US00PP21085P2

(12) United States Plant Patent

Klemm et al.

(10) Patent No.: US PP21,085 P2

(45) Date of Patent: Jun. 22, 2010

(54) *PELARGONIUM* PLANT NAMED 'KLEPZ08224'

(50) Latin Name: *Pelargonium zonale*
Varietal Denomination: KLEPZ08224

(75) Inventors: Nils Klemm, Stuttgart (DE); Martin Glawe, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 12/383,405

(22) Filed: Mar. 24, 2009

(51) Int. Cl.
*A01H 5/00* (2006.01)

(52) U.S. Cl. ..... Plt./330

(58) Field of Classification Search ..... Plt./330
See application file for complete search history.

*Primary Examiner*—Susan B McCormick Ewoldt
(74) *Attorney, Agent, or Firm*—Jondle & Associates, P.C.

(57) ABSTRACT

A new cultivar of *Pelargonium* named 'KLEPZ08224' particularly characterized with shiny red inflorescences, an upright plant habit with a medium growth habit, and good flower quality, is disclosed.

1 Drawing Sheet

Genus and species: *Pelargonium zonale.*
Variety denomination: 'KLEPZ08224'.

BACKGROUND OF THE NEW PLANT

The present invention comprises a new and distinct cultivar of *Pelargonium*, botanically known as *Pelargonium zonale*, and hereinafter referred to by the cultivar name 'KLEPZ08224'. 'KLEPZ08224' was discovered as a seedling resulting from a cross in June 2004 in Stuttgart, Germany between the proprietary female *Pelargonium* parent, 'KLEP03107' (U.S. Plant Pat. No. 18,025) and the proprietary male *Pelargonium* parent, 'S 010' (unpatented). A single plant selection was subsequently chosen for further evaluation and for asexual propagation.

The new cultivar was created in 2004 and first propagated in August 2005 in Stuttgart, Germany and has been asexually reproduced repeatedly by vegetative cuttings in Stuttgart, Germany over a four year period. 'KLEPZ08224' has been found to retain its distinctive characteristics through successive asexual propagations.

Plant Breeder's Rights for this cultivar were applied for in Switzerland on Jun. 19, 2008 and in Canada on Mar. 28, 2008. 'KLEPZ08224' has not been made publicly available more than one year prior to the filing date of this application.

SUMMARY OF THE INVENTION

The following are the most outstanding and distinguishing characteristics of this new cultivar when grown under normal commercial practices in a greenhouse in Stuttgart, Germany.

1. Shiny red inflorescences;
2. An upright plant habit with a medium growth habit; and
3. Good flower quality.

DESCRIPTION OF THE PHOTOGRAPH

This new *Pelargonium* plant is illustrated by the accompanying photograph which shows blooms, buds, and foliage of the plant; the colors shown are as true as can be reasonably obtained by conventional photographic procedures.

The photograph is of a plant about 3-months old taken in Spring 2008 and grown from rooted cuttings in a 12-cm pot under greenhouse (glasshouse) in Stuttgart, Germany under conditions which approximate those generally used in commercial practice.

DESCRIPTION OF THE NEW CULTIVAR

The following detailed descriptions set forth the distinctive characteristics of 'KLEPZ08224'. The data which define these characteristics were collected from asexual reproductions carried out in Stuttgart, Germany. The plant history was taken on 3-month old, un-pinched plants in 12-cm pots in a greenhouse in January through April. The color readings were determined under natural light. Color references are to The R.H.S. Colour Chart of The Royal Horticultural Society of London (R.H.S.) (2001).

DETAILED BOTANICAL DESCRIPTION

Classification:
- *Family.*—Geraniacaea.
- *Species.*—*Pelargonium zonale.*
- *Common name.*—*Pelargonium* (*Geranium*).
- *Denomination.*—'KLEPZ08224'.

Parentage:
- *Female parent.*—The proprietary female *Pelargonium* parent, 'KLEP03107' (U.S. Plant Pat. No. 18,025).
- *Male parent.*—The proprietary male *Pelargonium* parent, 'S 010' (unpatented).

Plant:
- *Habit.*—Upright.
- *Height.*—16.0 cm.
- *Spread.*—25.0 cm.
- *Life cycle.*—Spring to autumn.
- *Form.*—Round, bushy.
- *Time to produce a rooted cutting.*—18 days.
- *Time to bloom from propagation.*—Approximately 77 days.
- *Lastingness of inflorescence on the plant.*—10 to 13 days.

Stems:
*Stem color.*—RHS 137C.
*Pubescence.*—Weak, short hairs.
*Pubescence color.*—Greenish white.
*Stem form.*—Round.
*Diameter.*—0.8 cm to 1.0 cm.
*Length.*—8.0 cm to 10.0 cm.
*Internode length.*—About 0.8 cm to 2.0 cm.
Leaves:
*Arrangement.*—Alternate.
*Shape.*—Kidney-shaped.
*Apex.*—Round.
*Base.*—Open.
*Margin.*—Entire.
*Surface appearance* (*both surfaces*).—Dull.
*Length.*—4.0 cm to 7.0 cm.
*Width.*—5.0 cm to 8.0 cm.
*Color.*—Upper surface: RHS 139A. Lower surface: RHS 137B.
*Surface texture* (*both surfaces*).—Pubescent.
*Petiole.*—Length: 2.0 cm to 8.0 cm. Color: RHS 137C.
*Venation pattern.*—Palmate.
*Venation color.*—RHS 137C.
Inflorescence:
*Flowering habit.*—Continuous.
*Umbels.*—Height: 8.0 cm to 10.0 cm. Diameter: 10.0 to 14.0 cm.
*Individual florets of the umbel.*—Depth: 1.5 cm to 2.0 cm. Diameter: 5.0 cm.
*Fragrance.*—Absent.
Flower buds:
*Cluster shape.*—Round-ovate.
*Length.*—1.0 cm to 3.0 cm.
Width.—1.0 cm to 4.0 cm.
*Texture.*—Smooth (not pubescent).
*Bud.*—Shape: Elliptic, shell-shaped. Apex: Acute. Base: Blunt. Margin: Entire, smooth. Color: RHS 137B. Size: Length: 0.8 cm to 1.5 cm. Width: 0.5 cm to 0.8 cm.
Petals:
*Quantity per flower.*—6 to 9.
*Shape.*—Drop-shaped.
*Apex.*—Round.
*Base.*—Obtuse.
*Margin.*—Entire.
*Length.*—2.5 cm.
*Width.*—2.5 cm.
*Color of lobes.*—Upper lobes (both surfaces): RHS 44A. Lower lobes (both surfaces): RHS 44B.
*Fragrance.*—Absent.
Sepals:
*Number per flower.*—5.
*Shape.*—Lanceolate.
*Apex.*—Acute.
*Base.*—Obtuse.
*Margin.*—Entire.
*Color* (*both surfaces*).—RHS 137B and RHS 178B at the base.
*Length.*—1.5 cm.
*Width.*—0.3 cm to 0.4 cm.
Pedicel:
*Length.*—2.5 cm.
*Diameter.*—0.15 cm.
*Color.*—RHS 176A.
Peduncle:
*Length.*—15.0 cm to 20.0 cm.
*Diameter.*—0.5 cm.
*Color.*—RHS 176A to RHS 176C and RHS 137C.
*Surface texture.*—Smooth (not pubescent).
Reproductive organs:
*Stamens.*—Anther length: 0.2 cm. Filament length: 0.5 cm to 0.7 cm. Filament color: RHS 65D and RHS 43D. Pollen amount: Moderate. Pollen color: RHS 32A.
*Pistils.*—Number: 1. Stigma color: RHS 46A. Style length: Small. Style color: RHS 137D. Ovary arrangement: Central, middle.
Fruit/seed set: None observed.
Disease and insect resistance: No particular disease or insect resistance observed.

COMPARISON WITH PARENTAL AND COMMERCIAL CULTIVARS

'KLEPZ08224' differs from the female parent, the proprietary female *Pelargonium* parent, 'KLEP03107' (U.S. Plant Pat. No. 18,025) in that 'KLEPZ08224' has a medium growth habit and a long peduncle, while 'KLEP03107' has a compact growth habit and a shorter peduncle.

'KLEPZ08224' differs from the male parent, the proprietary male *Pelargonium* parent, 'S 010' (unpatented) in that 'KLEPZ08224' has a weak leaf zonation and a medium growth habit, while 'S 010' (unpatented) has a weak to strong leaf zonation and a strong growth habit.

'KLEPZ08224' differs from the commercial comparison variety 'GRADORED' (U.S. Plant Pat. No. 18,695) in that 'KLEPZ08224' has an entire leaf margin, a short stem length (8.0 cm to 10.0 cm), and large umbels (height of 8.0 cm to 10.0 cm and diameter of 10.0 cm to 14.0 cm), while 'GRADORED' (U.S. Plant Pat. No. 18,695) has a dentate leaf margin, a long stem length (15.0 cm to 18.0 cm), and small umbels (height of 4.5 cm and diameter of 7.9 cm).

I claim:

1. A new and distinct cultivar of *Pelargonium* plant named 'KLEPZ08224' as shown and described herein.

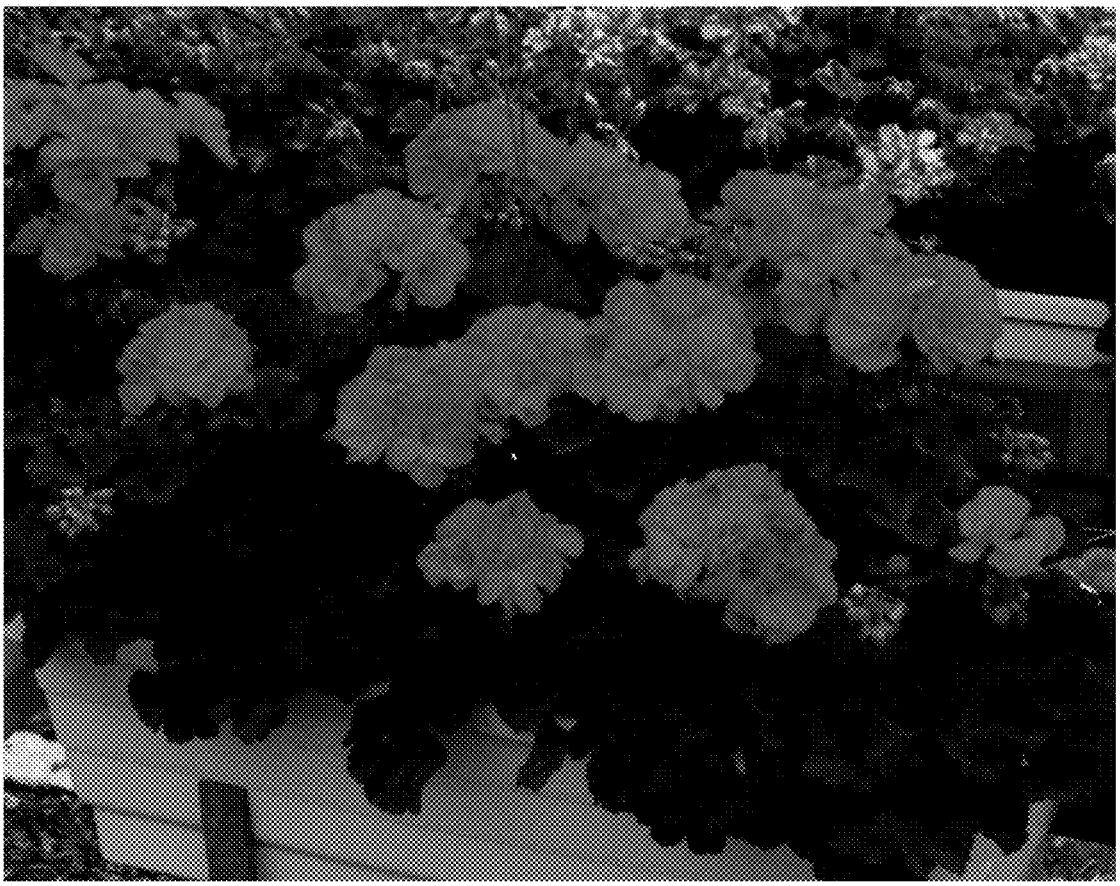

* * * * *